US012723202B2

(12) United States Patent
Zhou et al.

(10) Patent No.: US 12,723,202 B2
(45) Date of Patent: Sep. 1, 2026

(54) STEAM CRACKING METHOD UTILIZING ELECTRICITY FOR PROVIDING ENERGY

(71) Applicants: China University of Petroleum—Beijing, Beijing (CN); Beijing Carbon Zero Hydrogen Electric Technology Co., Ltd., Beijing (CN)

(72) Inventors: Hongjun Zhou, Beijing (CN); Quangui Wu, Beijing (CN); Hongmei Song, Beijing (CN); Fengyun Bi, Beijing (CN); Enze Zhou, Beijing (CN); Guanglin Zhou, Beijing (CN); Chunming Xu, Beijing (CN)

(73) Assignees: CHINA UNIVERSITY OF PETROLEUM-BEIJING, Beijing (CN); BEIJING CARBON ZERO HYDROGEN ELECTRIC TECHNOLOGY CO., LTD., Beijing (CN)

( * ) Notice: Subject to any disclaimer, the term of this patent is extended or adjusted under 35 U.S.C. 154(b) by 124 days.

(21) Appl. No.: 18/382,750

(22) Filed: Oct. 23, 2023

(65) Prior Publication Data

US 2024/0052247 A1 Feb. 15, 2024

Related U.S. Application Data

(63) Continuation of application No. PCT/CN2022/083721, filed on Mar. 29, 2022.

(30) Foreign Application Priority Data

Apr. 21, 2021 (CN) ........................ 202110429333.6
Jun. 3, 2021 (CN) ........................ 202110619015.6

(51) Int. Cl.
*C10G 9/24* (2006.01)
*C07C 4/04* (2006.01)
*C10G 15/08* (2006.01)

(52) U.S. Cl.
CPC .................. *C10G 9/24* (2013.01); *C07C 4/04* (2013.01); *C10G 15/08* (2013.01)

(58) Field of Classification Search
None
See application file for complete search history.

(56) References Cited

U.S. PATENT DOCUMENTS 4,740,290 A * 4/1988 Tomita .................... C01B 3/384 423/652
4,780,196 A * 10/1988 Alagy ...................... C10G 9/20 585/650
2006/0116543 A1* 6/2006 Bellet ...................... C10G 9/24 422/199

FOREIGN PATENT DOCUMENTS

BR PI1104399 A2 3/2016
CN 1358222 A 7/2002
(Continued)

OTHER PUBLICATIONS

Machine translation CN 103483124. retrieved May 23, 2025. (Year: 2025).*
(Continued)

*Primary Examiner* — Renee Robinson
*Assistant Examiner* — Alyssa L Cepluch
(74) *Attorney, Agent, or Firm* — LOZA & LOZA, LLP; Michael F. Fedrick

(57) ABSTRACT

The present invention provides a method of steam cracking using electricity to supply energy. This method is to provide energy for steam cracking reaction of a cracking raw material by electromagnetic induction with electricity; the cracking raw material comprises one or more of naphtha, cycloal-
(Continued)

kane and cycloolefin; wherein the cycloalkane is a C4-C8 cycloalkane, and the cycloolefin is a C4-C8 cycloolefin. The present invention utilizes electricity to provide energy for the steam cracking reaction through an electromagnetic coil, which is a new use of electricity and solve the current problem of excess electricity. Moreover, utilizing the electromagnetic coil to provide power can make the heat distribution in the furnace tube of the cracking furnace more uniform, and it is easier to control the reaction temperature and the progress of the reaction.

9 Claims, 1 Drawing Sheet

(56) References Cited

FOREIGN PATENT DOCUMENTS

| | | | | |
|---|---|---|---|---|
| CN | 103483124 | A | * | 1/2014 |
| CN | 103483127 | A | | 1/2014 |
| CN | 103588608 | A | * | 2/2014 |
| CN | 104449803 | A | | 3/2015 |
| CN | 108246210 | A | | 7/2018 |
| CN | 208145921 | U | | 11/2018 |
| CN | 110170280 | A | | 8/2019 |
| CN | 111099948 | A | | 5/2020 |
| CN | 111100685 | A | | 5/2020 |
| CN | 113307715 | A | | 8/2021 |
| CN | 113845089 | A | | 12/2021 |
| CN | 215517509 | U | | 1/2022 |
| FR | 2525122 | A1 | | 10/1983 |
| GB | 596879 | A | | 1/1948 |
| JP | H09235564 | A | | 9/1997 |

OTHER PUBLICATIONS

Machine translation CN 103588608. retrieved May 23, 2025 (Year: 2025).*

Haimbaugh "Induction Heat Treating Systems" ASM Handbook vol. 4B, Steel Heat Treating Technologies. 2014. pp. 197 and 205-206. (Year: 2014).*

International search report issued for corresponding International Patent Application No. PCT/CN2022/083721 mailed on Jun. 24, 2022.

First Office Action and search report issued on Mar. 14, 2023 for counterpart Chinese Patent Application No. 202110619015.6 with machine translation.

Li Ling et al., "Feasibility Study of new type Pyrolysis Liquefacient Reactor Based on Electromagnetic Induction," Energy Research & Utilization, Mar. 31, 2009, pp. 23-26.

Xu Hou, et al., "Role of normal/cyclo-alkane in hydrocarbons pyrolysis process and product distribution", Journal of Analytical and Applied Pyrolysis, vol. 156, 105130 (2021), 13 pages.

Extended European Search Report issued on Feb. 27, 2025 for counterpart European Patent Application No. 22790817.5, 18 pages.

* cited by examiner

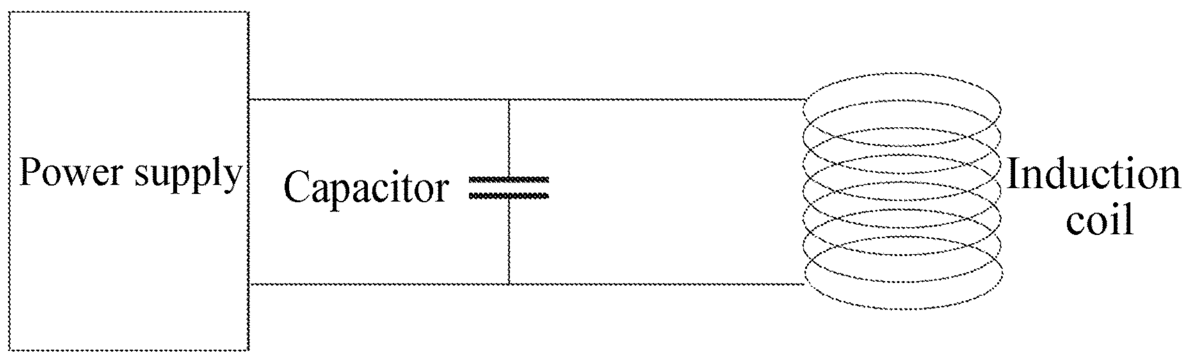
Power supply
Capacitor
Induction
coil

STEAM CRACKING METHOD UTILIZING ELECTRICITY FOR PROVIDING ENERGY

CROSS-REFERENCE TO RELATED APPLICATIONS

This application is a continuation of International Patent Application No. PCT/CN2022/083721, filed on Mar. 29, 2022, which claims the benefit of priority under 35 U.S.C. § 119 from Chinese Patent Application No. 202110429333.6, filed on Apr. 21, 2021, and from Chinese Patent Application No. 202110619015.6, filed on Jun. 3, 2021. The disclosures of the foregoing applications are incorporated herein by reference in their entireties.

FIELD OF THE INVENTION

The present invention relates to a steam cracking method using electricity to supply energy, and belongs to the technical field of comprehensive utilization of electrical energy.

BACKGROUND OF THE INVENTION

Massive carbon dioxide emissions and environmental pollution lead to climate warming and haze, threatening the survival of mankind and the health of the population. An effective solution is to decarbonize energy sources and reduce fossil energy consumption, especially the use of coal, while developing and using renewable energy sources, especially green sources of electricity such as photovoltaic, wind and hydropower.

Unlike fossil energy sources such as coal, oil and natural gas, which can be easily stored, electricity must be produced, transmitted and utilized simultaneously online. This feature determines that for electricity as an energy source, the core characteristics of its time dimension must be taken into account and the relationship between the power supply, electricity and consumption end must be coordinated with the aim of achieving synchronization. The disconnection of any party will affect the overall situation of electricity.

At present, the production of renewable energy such as photovoltaics, wind power, and hydropower is often spatially mismatched with the consumption side, resulting in a contradiction between the production, transmission and consumption of electricity. For example, photovoltaic, wind power and hydropower resources are mainly distributed in the northwest and southwest, while the energy consumption end is concentrated in the eastern coastal areas, with thousands of kilometers away from each other. Through the long-distance transmission of electricity is one of the solutions to solve the above problems. Single long-distance output also has the problem of coordination among production, transmission and consumption, and there are problems such as output fluctuation and poor economy, which are difficult to be absorbed. Therefore, a large amount of electricity generated in the west cannot be exported to the east over long distances, and there are no suitable local consumption scenarios, resulting in the abandonment of a large amount of wind, water and light.

Electricity production must effectively address the two major challenges of local consumption and controllable load fluctuations. Through on-site energy storage devices (such as photovoltaic farms with energy storage) can only solve the peak shifting and controllable loads, it is still difficult to solve the problem of consumption, not to mention that the current energy storage technology is difficult to realize the low-cost storage of large-scale power.

Therefore, to find a new way out for electricity is an urgent technical problem that is needed to be solved in the field of electric power.

SUMMARY OF THE INVENTION

In order to solve the above technical problems, an object of the present invention is to provide a method of consuming and utilizing electrical energy. The electrical energy is used for the steam cracking function of hydrocarbons, providing a completely new idea for the utilization of electrical energy.

In order to achieve the above object, the present invention provides a method of steam cracking using electricity to supply energy. The method includes supplying energy for steam cracking reaction of a cracking raw material with electricity by electromagnetic induction; wherein the cracking raw material comprises one or more of naphtha, cycloalkane and cycloolefin; wherein the cycloalkane is a C4-C8 cycloalkane, and the cycloolefin is a C4-C8 cycloolefin.

According to a specific embodiment of the present invention, preferably, the supplying energy is carried out by heating the steam cracking reaction tube by means of an induction coil, and supplying the cracking raw material with heat from the reaction tube. After the induction coil is supplied with power, electromagnetic induction is generated between the steam cracking reaction tube and the induction coil, and the steam cracking reaction tube generates heat, thereby realizing the heating of the cracking raw material inside the steam cracking reaction tube. In the process, the induction coil is preferably wrapped around the outside of the steam cracking reaction tube, and a thermal insulation material (e.g., cement, fireproof material, etc.) can be filled between the reaction tube and the induction coil. Conventional steam cracking devices are provided with heat through combustion of fuel oil and gas, and then the reaction tube is heated through heat exchange with the reaction tube to realize the heating of the reaction tube, and thus the cracking raw material is heated in the reaction tube. However, such heat exchange tends to be not uniform, and the heat would be concentrated in a local area, resulting in that the cracking reaction is also not uniform. The present invention, on the other hand, heats the reaction tube by means of an induction coil, which has a high heating efficiency, and the induction coil is uniformly distributed on the reaction tube, such that the reaction tube uniformly generates electromagnetic induction, and realizes uniform heating of the cracking raw material.

According to a specific embodiment of the present invention, preferably, the frequency of the current inputted into the induction coil is medium frequency or high frequency to meet the needs of electromagnetic induction as well as controlling the reaction temperature. During the process of implementation, the frequency of the control current can be selected according to the desired reaction temperature. The high frequency is 5-20 KHz, preferably 8-16 KHz, more preferably 10-15 KHz, further preferably 12-14 KHz, and specifically may be 8 KHz, 8.5 KHz, 9 KHz, 9.5 KHz, 10 KHz, 10.5 KHz, 11 KHz, 11.5 KHz, 12 KHz, 12.5 KHz, 13 KHz, 13.5 KHz, 14 KHz, 14.5 KHz, 15 KHz, 15.5 KHz, 16 KHz, or it may be a range obtained by combining the endpoints of the above ranges as well as the enumerated specific frequency values with each other, such as 5-16 KHz, 5-15 KHz, 5-10 KHz, 8-20 KHz, 8-15 KHz, 8-10 KHz, 10-20 KHz, 10-16 KHz, 10-12 KHz, 9-20 KHz, 9-15 KHz, 12-15 KHz, 12-14 KHz, 12-20 KHz; the medium frequency is 50-3000 Hz, preferably 300-2000 Hz, more preferably 600-1500 Hz, and specifically may be 300 Hz, 400 Hz, 500

Hz, 600 Hz, 700 Hz, 800 Hz, 900 Hz, 1000 Hz, 1100 Hz, 1200 Hz, 1300 Hz, 1400 Hz, 1500 Hz, 1600 Hz, 1700 Hz, 1800 Hz, 1900 Hz, 2000 Hz, or it may be a range obtained by combining the endpoints of the above ranges as well as the enumerated specific frequency values with each other, such as 300-3000 Hz, 300-1500 Hz, 600-3000 Hz, 600-2000 Hz, 1000-3000 Hz, 1000-2000 Hz, 1200-3000 Hz, 1200-2000 Hz, 1500-3000 Hz, 1500-2000 Hz, and the like.

According to a specific embodiment of the present invention, preferably, the frequency of the current inputted into the induction coil is regulated by a power supply and a capacitor. The induction coil is connected to the power supply to form a circuit, and the power supply is connected in parallel with the capacitor as shown in FIG. 1. The power supply used in the present invention may be a commonly used industrial power supply, such as a medium frequency power supply or a high frequency power supply. The power and other specification parameters of the power supply can be selected according to the frequency that needs to be adjusted to, and the rated power of the power supply is preferably 100-1000 KW, and more preferably 200-500 KW. The specification of the capacitor can also be selected as desired, as long as it is sufficient to be able to be matched with the power supply to meet the frequency control requirements.

According to a specific embodiment of the present invention, preferably, the induction coil is one or more of a ferrite coil, an iron core coil, a hollow coil, a copper core coil, and the like.

According to a specific embodiment of the present invention, preferably, the cracking raw material of the present invention comprises cycloalkane and/or cycloolefin; preferably, the cycloalkane is a C4-C8 cycloalkane, more preferably cyclohexane; the cycloolefin is a C4-C8 cycloolefin, more preferably cyclohexene.

According to a specific embodiment of the present invention, preferably, the cracking raw material is a cracking raw material containing cyclohexene and/or cyclohexane; the cracking raw material may be entirely cyclohexene and/or cyclohexane, or it may be a raw material partially containing cyclohexene and/or cyclohexane (e.g., naphtha, liquefied petroleum gas, etc.), i.e. the total content of cyclohexene and cyclohexane of the cracking raw material may be 80% or more, preferably 90% or more, more preferably 100%. Steam cracking with cracking raw materials containing cyclohexene and cyclohexane may provide products such as butadiene.

According to a specific embodiment of the present invention, in the cracking raw material, in particular when the cracking raw material consists entirely of cyclohexene and cyclohexane, the weight ratio of cyclohexane to cyclohexene is preferably from 2:8 to 8:2; more preferably from 3:7 to 7:3; and further preferably from 3:7 to 5:5, for example, 3:7, 4:6, 5:5.

According to a specific embodiment of the present invention, when the cracking raw material is pure cyclohexene, the yield of 1,3-butadiene may be up to 36% or more, and the total yield of triene may be up to 89% or more; when the cracking raw material is pure cyclohexane, the yield of 1,3-butadiene may be up to 27% or more, and the total yield of triene may be up to 68% or more; when the cracking raw material is a combination of cyclohexane and cyclohexene in a mass ratio of 3:7 to 7:3, the yield of 1,3-butadiene may be up to 19% or more, and the total yield of triene may be up to 61% or more; when the cracking raw material is a combination of cyclohexane and cyclohexene in a mass ratio of less than 3:7 (i.e., cyclohexene is dominant), the yield of 1,3-butadiene may be up to 31% or more, and the total yield of triene may be up to 74% or more.

According to a specific embodiment of the present invention, the reaction temperature of the steam cracking reaction is preferably controlled to be 500-1200° C., more preferably 700-900° C., further preferably 750-850° C.

According to a specific embodiment of the present invention, preferably, the steam cracking reaction has a water-oil ratio of 0.3-0.7, preferably 0.4-0.5.

According to a specific embodiment of the present invention, the residence time is preferably controlled to be 0.1-1 s, more preferably 0.3-0.8 s, further preferably 0.4-0.7 s.

According to a specific embodiment of the present invention, the size of the steam cracking reaction tube used in the present invention can be selected as desired, wherein the inner diameter of the steam cracking reaction tube can be 50-250 mm and the length can be selected according to the reaction requirement.

According to a specific embodiment of the present invention, the material of the steam cracking reaction tube may be a metal or an alloy, including but not limited to the materials typically used for reaction tubes for steam cracking reaction. The metal or alloy is preferably one capable of withstanding a temperature of 1000° C., more preferably one capable of withstanding a temperature of 1200° C. The material of the steam cracking reaction tube of the present invention may be selected from 316L stainless steel, 304S stainless steel, HK40 high-temperature furnace tube material, HP40 high-temperature furnace tube material, HP Micro Alloy micro-alloy steel, Manaurite XTM material for steam cracking furnace, or the like.

The present invention utilizes electricity to provide energy for the steam cracking reaction through an electromagnetic coil, which is a new use of electricity and solve the current problem of excess electricity. Moreover, utilizing the electromagnetic coil to provide power can make the heat distribution in the furnace tube of the cracking furnace more uniform, and it is easier to control the reaction temperature and the progress of the reaction.

The apparatus employed for conventional steam cracking (e.g., preparation of butadiene from cyclohexane and cyclohexene as feedstock by steam cracking) may comprise a cracking furnace and a separation unit. The cracking furnace may be a cracking furnace commonly used in the field for production of ethylene and butadiene by steam cracking, and it generally comprises a convection section, a radiation section, an emergency cooling boiler, and a fuel system (e.g., a fuel gas system or a fuel oil system). In this cracking furnace, the cracking raw material and steam pass sequentially through the sections along the cracking furnace tubes (or steam cracking reaction tubes) and are heated in the convection section and the radiation section until a steam cracking reaction occurs, generating cracked gas; the cracked gas leaves the radiation section and enters the rapid cooling boiler, where the cracked gas is cooled down to 300-600° C. to keep the cracked gas from undergoing a cracking reaction and to recover the heat; the fuel system is used to supply heat to the steam cracking reaction process; and the separation unit can be selected from conventional separators, depending on the requirements of the composition and separation of the cracked gas. As can be seen from the above, traditional steam cracking supplies energy by using gas and fuel oil, and the energy utilization rate is relatively low (the energy conversion rate of fuel gas and fuel oil is generally 30-40%). It requires heat recovery treatment, and has more equipment, high investment, high pollution and high carbon emission. In contrast, the method provided by the present invention supplies energy for steam cracking by electromagnetic induction, which can omit the huge cracker furnace body and fuel system. It is only necessary to add electromagnetic coils outside the reaction tube and set up corresponding power supply equipment according to the frequency needs. This allows for low investment and no pollution or carbon emissions. In particular, the conversion rate is relatively high and can generally be as much as 90% or more.

The present invention applies electrical energy to the reaction of cyclohexane, cyclohexene, and the like, for the preparation of 1,3-butadiene by steam cracking. The yield of 1,3-butadiene may be up to 19% or more, and the total yield of triene may be up to 60% or more, which are significantly higher than that of the conventional steam cracking process. Moreover, with the technical solution of the present invention, there are no carbon dioxide emissions during the steam cracking process, which is not achievable with existing steam cracking processes.

BRIEF DESCRIPTION OF THE DRAWINGS

FIG. 1 shows a schematic circuit diagram of the power supply, electromagnetic coil, and capacitor of the present invention.

DETAILED DESCRIPTION OF PREFERRED EMBODIMENTS

In order to have a clearer understanding of the technical features, objectives and beneficial effects of the present invention, the following detailed description of the technical solutions of the present invention is given, but it is not to be understood as limiting the implementable scope of the present invention.

Example 1

The example provides a method of steam cracking powered by electricity, which is carried out using the device shown in FIG. 1. The device includes a power supply (300 KW medium-frequency power supply), a capacitor (matching with the medium-frequency power supply), an induction coil (copper-core coil, 30 cm in length, wrapped around the outside of the reaction tube) and a steam cracking reaction tube (316L stainless steel, 30 cm in length, 1.7 cm in inner diameter), wherein the induction coil is connected to the power supply to form a circuit, and the power supply is connected in parallel with the capacitor. The power supply is used to adjust the electricity to a current of appropriate frequency, which is then input into the capacitor, through which the induction coil is powered. Electromagnetic induction generated between the steam cracking reaction tube and the energized induction coil starts generating heat, which heats up the steam cracking raw material inside the reaction tube in order to allow the steam cracking reaction to take place.

In this example, cyclohexene, cyclohexane, a mixture of cyclohexene and cyclohexane, and industrial cyclohexane samples are used as cracking raw materials for the steam cracking reaction, respectively, wherein the industrial cyclohexane samples comprise naphtha sample produced as a by-product of coal-to-liquid production and reformed raffinate oil samples. The physical parameters of them are shown in Tables 1 and 2, respectively. The reaction conditions and reaction results are shown in Table 3.

TABLE 1

Physical parameters of naphtha samples produced as a by-product of coal-to-liquid production

| Density | Initial distillation point | 10% | 50% | 90% | Final distillation point | Total distillation |
|---|---|---|---|---|---|---|
| kg/m$^3$ | ° C. | ° C. | ° C. | ° C. | ° C. | ml |
| 760-790 | 78 | 90 | 101 | 119 | 150 | 98 |

TABLE 2

Physical parameters of reformed raffinate oil samples

| Density | Initial distillation point | 10% | 50% | 90% | Final distillation point | Total distillation |
|---|---|---|---|---|---|---|
| kg/m$^3$ | ° C. | ° C. | ° C. | ° C. | ° C. | ml |
| 678.5 | 67 | 69 | 74 | 85 | 99 | 98 |
| 678.3 | 66 | 70 | 74 | 83 | 106 | 99 |

The data in Table 2 are the results of the tests under two different experiments.

TABLE 3

| | Reaction conditions | | | | | | | |
|---|---|---|---|---|---|---|---|---|
| Cracking raw materials | Water-oil ratio | Voltage V | Current A | Power KW | Frequency KHz | Reaction temperature ° C. | Residence time s | Sampling time |
| Cyclohexene | 0.5 | 72.89 | 9.49 | 1.12 | 13.3 | 800 | 0.4 | 1 h |
| (analytically pure) | 0.5 | 74.23 | 9.54 | 1.09 | 13.4 | | 0.4 | 1.5 h |
| Cyclohexane: | 0.5 | 77.00 | 9.72 | 1.12 | 13.0 | 750 | 0.4 | 1 h |
| cyclohexene | 0.5 | 77.00 | 9.72 | 1.12 | 13.2 | | 0.4 | 1.5 h |
| (mass ratio 3:7) | 0.5 | 77.00 | 9.72 | 1.2 | 13.1 | 800 | 0.4 | 3 h |
| | 0.5 | 77.00 | 9.72 | 1.2 | 13.2 | | 0.4 | 3.5 h |
| | 0.5 | 77.00 | 9.89 | 1.24 | 13.0 | 850 | 0.4 | 5 h |
| | 0.5 | 75.62 | 9.72 | 1.2 | 13.2 | | 0.4 | 5.5 h |
| Cyclohexane: | 0.5 | 72.89 | 9.49 | 1.09 | 13.4 | 750 | 0.4 | 1.5 h |
| cyclohexene | 0.5 | 72.89 | 9.49 | 1.2 | 13.5 | | 0.4 | 2 h |
| (mass ratio 5:5) | 0.5 | 74.23 | 9.72 | 1.12 | 13.2 | 800 | 0.4 | 3.5 h |
| | 0.5 | 74.23 | 9.72 | 1.09 | 13.3 | | 0.4 | 4 h |
| Cyclohexane: | 0.5 | 77.00 | 9.66 | 1.27 | 13.2 | 750 | 0.4 | 1 h |
| cyclohexene | 0.5 | 77.00 | 9.66 | 1.16 | 13.1 | | 0.4 | 1.5 h |
| (mass ratio 7:3) | 0.5 | 78.39 | 9.95 | 1.12 | 13.1 | 800 | 0.4 | 2.5 h |
| | 0.5 | 78.39 | 9.95 | 1.12 | 13.0 | | 0.4 | 3 h |

TABLE 3-continued

| | | | | | | | | |
|---|---|---|---|---|---|---|---|---|
| | 0.5 | 77.00 | 9.83 | 1.2 | 13.3 | 850 | 0.4 | 4 h |
| | 0.5 | 77.00 | 9.83 | 1.27 | 13.4 | | 0.4 | 4.5 h |
| Cyclohexane | 0.5 | 63.24 | 8.05 | 0.8 | 13.4 | 800 | 0.4 | 1 h |
| (analytically pure) | 0.5 | 63.24 | 8.05 | 0.8 | 13.3 | | 0.4 | 1.5 h |
| Huidong | 0.4 | 75.62 | 9.66 | 1.01 | 13.1 | 800 | 0.7 | 2 h |
| Cyclohexane | 0.4 | 75.62 | 9.72 | 1.01 | 13.3 | | 0.7 | 3 h |
| | 0.4 | 77.00 | 9.89 | 1.01 | 13.1 | 850 | 0.7 | 1 h 40 mi |
| | 0.4 | 27.49 | 1.84 | 0.71 | 13.2 | | 0.7 | 2 h |
| Yatong | 0.4 | 77.00 | 9.77 | 1.27 | 13.1 | 800 | 0.7 | 1 h |
| Cyclohexane | 0.4 | 77.00 | 9.77 | 1.16 | 13.2 | | 0.7 | 1.5 h |
| (reformed | 0.4 | 77.00 | 9.89 | 1.2 | 13.4 | 850 | 0.7 | 2.5 h |
| raffinate oil) | 0.4 | 77.00 | 9.95 | 1.2 | 13.3 | | 0.7 | 3 h |

| | Products | | | | | | |
|---|---|---|---|---|---|---|---|
| Cracking raw materials | Methane | Ethane | Ethylene | Propane | Propylene | Butene | Total trienes |
| Cyclohexene | 3.4974 | 1.4469 | 47.2171 | 0.1012 | 3.1516 | 39.4092 | 89.7779 |
| (analytically pure) | 3.5458 | 1.3643 | 49.7403 | 0.0454 | 3.0688 | 36.2263 | 89.0354 |
| Cyclohexane: | 3.1279 | 1.9498 | 42.489 | 0.0453 | 3.9374 | 39.3554 | 85.7818 |
| cyclohexene | 3.3194 | 2.127 | 38.9112 | 0.0937 | 3.9615 | 37.3018 | 80.1745 |
| (mass ratio 3:7) | 3.0191 | 1.524 | 38.5642 | 0.0503 | 3.75 | 38.7742 | 81.0884 |
| | 3.9027 | 1.8915 | 41.0005 | 0.057 | 4.0237 | 34.1912 | 79.2154 |
| | 4.4708 | 2.0958 | 38.7481 | 0.0512 | 3.4374 | 32.6918 | 74.8773 |
| | 5.0244 | 2.0881 | 39.5009 | 0.0567 | 3.5109 | 31.2597 | 74.2715 |
| Cyclohexane: | 3.5636 | 2.2053 | 38.5089 | 0.0603 | 5.0733 | 37.4382 | 81.0224 |
| cyclohexene | 3.2405 | 2.047 | 34.1241 | 0.0564 | 4.6804 | 36.91 | 75.7145 |
| (mass ratio 5:5) | 5.1709 | 2.5124 | 37.8757 | 0.0711 | 4.8495 | 28.691 | 21.4162 |
| | 5.0284 | 2.3579 | 34.062 | 0.0643 | 4.2468 | 22.9179 | 61.2267 |
| Cyclohexane: | 9.046 | 6.4634 | 36.6466 | 0.2396 | 10.7173 | 22.5383 | 69.9022 |
| cyclohexene | 8.789]1 | 6.3974 | 35.7076 | 0.2365 | 10.7589 | 21.7985 | 68.265 |
| (mass ratio 7:3) | 4.6004 | 3.0648 | 32.8679 | 0.0666 | 5.2291 | 23.0243 | 61.1213 |
| | 4.7071 | 3.5438 | 35.3197 | 0.1005 | 6.7098 | 24.1722 | 66.2017 |
| | 6.4373 | 3.5144 | 40.671 | 0.0755 | 5.4114 | 20.7051 | 66.7875 |
| | 6.8628 | 3.3383 | 41.3017 | 0.0732 | 5.1064 | 19.4559 | 65.864 |
| Cyclohexane | 4.4699 | 4.3835 | 34.4622 | 0.0797 | 9.9466 | 27.1383 | 71.5471 |
| (analytically pure) | 4.0814 | 4.0981 | 32.0438 | 0.0809 | 9.2811 | 27.2341 | 68.559 |
| Huidong | 16.9915 | 5.9973 | 24.9578 | 0.7405 | 20.3573 | 13.2808 | 58.5959 |
| Cyclohexane | 21.4102 | 7.2942 | 29.5447 | 0.8218 | 20.1825 | 8.6577 | 58.3849 |
| | 25.1457 | 4.8292 | 40.4643 | 0.253 | 10.2572 | 11.2306 | 61.9521 |
| | 25.1152 | 4.2494 | 39.7559 | 0.2788 | 12.0778 | 11.1931 | 63.0268 |
| Yatong | 25.1589 | 5.0748 | 32.0324 | 0.6008 | 14.5279 | 3.5826 | 50.1429 |
| Cyclohexane | 26.7583 | 5.437 | 35.1806 | 0.4871 | 12.2206 | 3.2053 | 50.6065 |
| (reformed | 31.8051 | 4.0287 | 42.8874 | 0.2183 | 6.6009 | 3.1222 | 52.6105 |
| raffinate oil) | 32.7209 | 3.7536 | 43.5557 | 0.1649 | 5.5012 | 2.9457 | 52.0026 |

CN103588608A discloses a method for the preparation of butadiene by steam cracking using cyclohexene and naphtha as raw materials, and in the case where pure cyclohexene is used as the cracking raw material, the yield of butadiene only reaches 13.51%. As can be seen from Table 3, by using electromagnetic induction to apply electrical energy to the steam cracking of cyclohexane and cyclohexene, the yield of 1,3-butadiene can reach more than 19%, and the total yield of triene can reach more than 60%, which are significantly higher than that of the conventional steam cracking process.

TABLE 4

| Parameter upper limits under industrial electricity conditions | | | |
|---|---|---|---|
| Power | Voltage | Current | Frequency |
| 200 KW | 3-phase 380 V | 305 A | 5-20 KHz |
| 300 KW | 3-phase 380 V | 455 A | 5-20 KHz |
| 500 KW | 3-phase 380 V | 760 A | 5-20 KHz |
| 200 KW | 3-phase 220 V | 530 A | 5-20 KHz |
| 300 KW | 3-phase 220 V | 790 A | 5-20 KHz |
| 500 KW | 3-phase 220 V | 1320 A | 5-20 KHz |

The voltage, current and power given in Table 3 are parameters under experimental conditions. In industrial applications, the size of the reaction tube, and the like, will be larger, and the degree of reaction and experimental conditions will be different. Industrial electricity is generally 220V three-phase or 380V three-phase, and the current and power can be adjusted according to the actual situation (Table 4 shows the upper limit of the parameters under industrial electricity conditions). This difference in parameters will not bring substantial difference to the products.

The invention claimed is:

1. A method of steam cracking comprising supplying energy to a cracking raw material by electromagnetic induction, comprising:

steam cracking the cracking raw material by heating a steam cracking reaction tube by means of an induction coil wrapped around outside the steam cracking reaction tube;

wherein a frequency of a current inputted into the induction coil is 5-20 KHz;

wherein conditions for the steam cracking include a reaction temperature of 500-1,200° C., a steam to hydrocarbon ratio of 0.3-0.7, and a residence time of 0.1-1 seconds; and wherein a cracking raw material comprises cyclohexene and cyclohexane in a weight ratio of cyclohexane to cyclohexene of 3:7.

2. The method according to claim 1, wherein the frequency of the current inputted to the induction coil is regulated by a power supply and a capacitor.

3. The method according to claim 2, wherein the induction coil is connected to the power supply to form a circuit, and the power supply is connected in parallel with the capacitor.

4. The method according to claim 2, wherein the power of the power supply is 100-1,000 kW.

5. The method according to claim 1, wherein the induction coil is one or more of a ferrite coil, an iron core coil, a hollow coil, and a copper core coil.

6. The method according to claim 1, wherein the steam cracking reaction tube has an inner diameter of 50-250 mm.

7. The method according to claim 1, wherein the steam cracking reaction tube is made of a metal or alloy.

8. The method according to claim 7, wherein the metal or alloy is a metal or alloy capable of withstanding a temperature of 1,000° C.

9. The method according to claim 7, wherein the metal or alloy is selected from 316L stainless steel, 304S stainless steel, HK40 high-temperature furnace tube material, HP40 high-temperature furnace tube material, HP Micro Alloy micro-alloy steel or Manaurite XTM material for steam cracking furnace.

* * * * *